United States Patent [19]

Hamilton et al.

[11] Patent Number: 5,236,705
[45] Date of Patent: Aug. 17, 1993

[54] FIBRINOLYSIS

[75] Inventors: John A. Hamilton, Kew; Prudence H. Hart, Millswood, both of Australia

[73] Assignee: The University of Melbourne, Melbourne, Australia

[21] Appl. No.: 720,868

[22] PCT Filed: Jan. 19, 1990

[86] PCT No.: PCT/AU90/00013
§ 371 Date: Sep. 18, 1991
§ 102(e) Date: Sep. 18, 1991

[87] PCT Pub. No.: WO90/07932
PCT Pub. Date: Jul. 26, 1990

[30] Foreign Application Priority Data
Jan. 20, 1989 [AU] Australia .................. PJ2356

[51] Int. Cl.$^5$ .............. A61K 45/00; A61K 37/48; A61K 37/54; A61K 37/62
[52] U.S. Cl. .............. 424/85.2; 424/94.63; 424/94.64
[58] Field of Search .................. 424/85.2

[56] References Cited

FOREIGN PATENT DOCUMENTS

| | | |
|---|---|---|
| 0230107 | 9/1987 | European Pat. Off. |
| 0333523 | 9/1989 | European Pat. Off. |
| WO8702990 | 5/1987 | World Int. Prop. O. |
| WO8707303 | 12/1987 | World Int. Prop. O. |
| WO8804667 | 6/1988 | World Int. Prop. O. |
| WO8909621 | 10/1989 | World Int. Prop. O. |

Primary Examiner—Christine M. Nucker
Assistant Examiner—Choon P. Koh
Attorney, Agent, or Firm—Walter H. Dreger

[57] ABSTRACT

A method for degrading fibrin deposits and preventing such deposits associated with pathological conditions is described, which comprises administering to a subject in need of such treatment a therapeutically effective amount of IL-4 activity, optionally in association with one or more pharmaceutically acceptable carriers or excipients. There is also described thrombolytic compositions which comprise IL-4 or a derivative thereof possessing IL-4 activity together with a pharmaceutically acceptable carrier or excipient.

13 Claims, No Drawings

FIBRINOLYSIS

The present invention relates to fibrin degradation or breakdown (which may be referred to as fibrinolysis), and compositions and methods for the treatment of pathological conditions associated with fibrin deposition.

Fibrin plays a crucial role in haemostasis and wound healing, and is laid down in the human and animal body as a result of a complex series of biochemical reactions. Notwithstanding these crucial functions of fibrin, fibrin formation is also a common event in many pathological conditions and inflammatory lesions. For example, fibrin deposition is associated with atherosclerosis, rheumatoid arthritis, glomerulonephritis, systemic lupus erythematosis, myocardial infarcts, pulmonary embolism, deep vein thrombosis, autoimmune neuropathies, granulomatous disease, parasitic infections and allograft rejection. Metastases, or so called "secondary" tumours, have been linked with thromboembolism phenomona. The abundant fibrin deposited around some solid tumours in the stroma may serve as a cocoon that hinders lymphocytes, macrophages and other inflammatory cells from reaching tumours.

Fibrin deposition may also be associated with renal disease and hypertrophic scars and keloids. Fibrous adhesions are also a significant problem in post-operative surgery.

Urokinase and tPA (tissue plasminogen activator) are plasminogen activators (PA's) which have previously been used both experimentally and clinically to effect fibrin lysis, and in particular, the lysis or degradation of fibrin clots. Whilst effective in degrading fibrin, these molecules have attendant disadvantages. Urokinase activates plasminogen to give plasmin independently of the presence of fibrin (unlike tPA), and thus large amounts must be administered to effect fibrinolysis, this being expensive and causing unwanted bleeding. tPA has a short half life in vivo, and thus large quantities have to be administered over a long period of time, resulting in unwanted bleeding and expense.

It has now surprisingly been found that the lymphokine, interleukin-4 (IL-4), activates both human and animal cells to produce plasminogen activators, which results in fibrin degradation. Also, IL-4 inhibits the procoagulant activity of human monocytes resulting in decreased fibrin formation at the monocyte surface.

IL-4 is a lymphokine, which exhibits both B cell and T cell growth factor activities (published Australian Patent Application No. 67334/87). This lymphokine also exhibits suppressive activity, as it supresses human monocyte production of the cytokines IL-1, TNF, and suppression of $PGE_2$.

IL-4 has been purified to homogeneity, and the gene encoding this protein has been cloned allowing IL-4 to be produced in large amounts by recombinant DNA technology, as described in published Australian Patent Application No. 67334/87, in the name Schering-Biotech Corporation. IL-4 (human) is commercially available from a number of suppliers.

On the basis of IL-4's activity in suppressing cytokine production, it was most surprising that IL-4 was effective in stimulating plasminogen activator (PA) production, notably, t-PA and urokinase, by appropriate target cells.

In accordance with the present invention, there is provided a method for degrading fibrin deposits and preventing such deposits associated with pathological conditions or which may lead to such conditions, which comprises administering to a subject in need of such treatment a therapeutically effective amount of IL-4 or a derivative thereof possessing IL-4 activity, optionally in association with one or more pharmaceutically acceptable carriers or excipients.

Pathological conditions which may be treated in accordance with the invention are those which are caused wholly or at least in part by fibrin deposition. These include deep vein thrombosis, pulmonary embolism, renal disease, hypertrophic keloid scars, coronary infarction, metastasis, inflammation, disseminated intravascular coagulation, atherosclerosis, rheumatoid arthritis, glomerulonephritis, systematic lupus eryttematosis, autoimmune neuropathies, granulomatous disease, parasitic infection, allograft rejection, and other conditions associated with fibrin deposition. Administering IL-4 to subjects suffering from such conditions may result in increased plasminogen activator, particularly tPA and urokinase (prourokinase) production by target cells, causing activation of plasminogen and subsequent fibrin degradation. Also, fibrin formation in such patients may be lessened.

Notable cell types stimulated to produce t-PA when stimulated with IL-4 are the monocyte/macrophage cell types. Importantly, these cell types are often closely associated with thrombi and other fibrin deposits, and hence, when stimulated to produce plasminogen activators on contact with IL-4, may cause highly efficient localised fibrin degradation. This avoids the need to administer large amounts of plasminogen activator to a patient, hence reducing side effects of unwanted bleeding, and excess cost due to the administration of large amounts of plasminogen activator.

Endothelial cells may also be stimulated with IL-4 to produce urokinase (prourokinase). This is also of importance as fibrin deposits are generally associated with endothelial cells.

Other target cells within a human or animal subject may also be stimulated with IL-4 to effect fibrin degradation. A number of other target cells besides the monocyte may also loose their ability to produce procoagulant activity as a result of IL-4 action.

Preferably, the IL-4 employed in this invention is produced by recombinant DNA technology. Where human subjects are to be treated, it is of course desirable that the IL-4 is of human origin. Where animals are treated, animal IL-4 is preferred.

Any IL-4 derivative or analogue which possesses the B cell, T cell and mast cell stimulatory effects of IL-4, and other characteristic activities of IL-4, as described in published Australian Patent Application No. 67334/87 may be used in this invention. The precise nature of IL-4 derivatives or analogues is not of importance. Rather, the derivatives or analogues must possess the well defined biological activity of IL-4, and, must possess the ability to stimulate target cells such as macrophages/monocytes to produce plasminogen activators. Application No. 67334/87 mentioned above teaches methods for the production of IL-4 derivatives and analogues. As used in this specification the term IL-4 encompasses human IL-4, IL-4 of animal origin such as murine, ovine or bovine IL-4, and analogues or derivatives thereof which possess characteristic IL-4 activity. For convenience these molecules may be referred to hereinafter as "active material".

IL-4 may be administered in a convenient manner such as by the oral, intraveneous, intramuscular, subcutaneous, intraperitoneal, intranasal, intradermal or suppository routes.

IL-4 may also be administered to a human or animal subject by continuous infusion over a predetermined time period, for example, from 30 minutes to 24 hours. Administration may be by way of an intravenous catheter connected to an appropriate pump, or by gravity feed.

The amounts of and dosage regimes of IL-4 which are administered to a subject to effect fibrin degradation will depend on a number of factors such as the mode of administration, the nature of the condition being treated, the body weight of the subject being treated, and the judgement of the prescribing physician or veterinarian. Generally speaking, IL-4 may be administered in an amount between 0.1 µg to 2000 mg per kilogram of body weight per day. The quantity of active compound in a unit dosage such as a tablet or capsule may vary from about 0.1 µg to 100 mg.

IL-4 may be coated by, or administered with, a material to prevent its inactivation. For example, the active material may be administered in an adjuvant, co-administered with enzyme inhibitors or in liposomes. Adjuvants contemplated herein include resorcinols, nonionic surfactants such as polyoxyethylene oleyl ether and n-hexadecyl polyethylene ether. Enzyme inhibitors include pancreatic trypsin inhibitor, diisopropylfluorophosphate (DFP) and trasylol. Liposymes include water-in-oil-in-water P40 emulsions as well as conventional liposomes.

Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, sterile water, ethanol, polyol (for example, glycerol, propylene glycol and liquid polyethylene glycol and the like), suitable mixtures thereof, and vegetable oils. The proper fluidity can be maintained, for example, by the use of a coating such as lecithin, by the maintenance of the required particle size in the case of a dispersion, and by the use of surfactants. The preventions of the action of microorganisms can be brought about by various antibacterial and antifungal agents, for example, parabens, chlorobutanol, phenol, sorbic acid, thermerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active material in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When IL-4 is suitably protected as described above, the active compound may be orally administered, for example, with an inert diluent or with an edible carrier, or it may be enclosed in hard or soft shell gelatin capsule, or it may be compressed into tablets, or it may be incorporated directly with the food of the diet. For oral therapeutic administration, the active material may be incorporated with excipients and used in the form of ingestible tablets, buccal tablets, troches, capsules, elixirs, suspensions, syrups, wafers, and the like.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharamceutically pure and substantially non-toxic in the amounts employed. In addition, the active material may be incorporated into sustained-release preparations and formulations.

As used herein, the terms "pharmaceutically acceptable carrier" and "excipient" include any and all solvents, dispersion media, coatings, antibacterial and antifungal agents, isotonic and absorption delaying agents, and the like described above. The use of such carriers and excipients is well known in the art, see for example, Remington's Pharmaceutical Science and U.S. Pharmacopeia (1984); Mack Publishing Company, Easton, Pa.

The active material may also be administered in association with one or more anti-thrombolytic agents selected from, for example, tPA, prourokinase, urokinase or streptokinase. Potentiation of fibrinolytic activity may take place when IL-4 is administered with such agents.

The active material may also be administered in association with one or more anticoagulant agents, such as heparin, warfarin, aspirin, anisindione, phenindone and bishydroxy coumarin; and/or one or more vasodilators such as nitriles (for example, amylnitrile, nitroglycerin, sodium nitrile, isosorbide dinitrate), papaverine, nicotinic acid and cyclandelate. Anticoagulant and vasodilatory agents may improve access to thrombosis and other fibrin deposits thereby enhancing fibrin degradation.

The invention is also concerned in another aspect with thrombolytic compositions which comprise IL-4 in association with one or more pharmaceutically acceptable carriers or excipients; and which optionally include one or more anti-thrombolytic agents, and/or one or more anticoagulant agents, and/or one or more vasodilators, as described above.

The action of IL-4 in causing fibrin degradation and preventing fibrin and thrombi formation is surprising and unexpected based on the prior art known to the applicant, and provides new therapies for diseases associated with fibrin formation.

The following Examples further illustrate the invention. It will, of course, be understood that the invention is in no way restricted to the specific embodiments described in these Examples.

EXAMPLE 1

Materials and Methods

Monocyte Isolation and Culture

Monocytes were isolated from peripheral venous blood by countercurrent centrifugal elutriation as described by Hart et al. (1988) J. Immunol. 141: 1516. Cell fractions containing >95% monocytes, identified by morphological criteria, by non-specific esterase staining and by their phagocytic properties were pooled and cultured for 18 h as previously detailed ($0.8-1.0 \times 10^6$ in 1 ml α-Modified Eagle's Medium containing 1% fetal calf serum). To terminate the cultures, the supernatants were centrifuged to remove non-adherent cells; after twice washing with PBS, the adherent and non-adherent cells were pooled and lysed with 0.2% Triton X-100 in PBS.

Assay for PA Activity

Monocyte supernatants or lysates (50 μl) and human plasminogen (0.8 μg), dissolved in 100 μl 0.1M Tris-HCl, pH 8.1, were added to 0.28 cm$^2$ wells previously coated with $^{125}$I-fibrin, according to the methods of Hamilton (1981) J. Immunol. 126: 851. After 2-3 h, soluble $^{125}$I-fibrin degradation products were measured. PA activity was expressed according to the activity of u-PA standards (Leo Pharmaceutical Products, Denmark). Monocyte-derived plasminogen-independent fibrinolytic activity was always <5% of the plasminogen-dependent activity.

Antibody Analysis

IgGs (immunoglobulins) were isolated from rabbit antisera to human u-PA and to human t-PA (Lots 100 and 153, respectively provided by Dr. W-D. Schleuning, CHUV, Laus anne, Switzerland) by standard methods using Protein A Sepharose CL-4B (Pharmacia, Uppsala, Sweden). The mouse myeloma IgG, HOPCY (Dr. A. Burgess, Ludwig Institute for Cancer Research, Melbourne, Australia), was used as an irrelevant antibody. Culture supernatants, cell lysates or PA standards (u-PA) as above, t-PA as a culture supernatant rom the MM138 melanoma cell line (Dr. R. Whitehead, Ludwig Institute for Cancer Research, Melbourne), 0.2 IU/ml) were incubated with IgGs (1 μg/ml final concentration) for 1 h at 37° C. prior to assay of residual PA activity. In the immunoprecipitation experiments, Protein A Sepharose CL-4B was added, as well as Triton X-100 to a final concentration of 0.25%. After further incubation for 30 min. at room temperature with periodical mixing, the pellets were washed as previously described in Vassalli, J. D., et al. (1984) J. Exp. Med. 159: 1643, except that SDS was not included in the wash buffers.

SDS-Casein Zymography

SDS-PAGE zymography was carried out according to the methods of Roche et al. (1983) B.B.A. 745: 82. The resolving gel (10%) contained casein (2 mg/ml, Sigma) and human plasminogen (6 μg/ml) and was pre-electrophoresed at 15 mA for 1 h at room temperature. Samples (20 μl), equilibrated in 0.0625M Tris-HCl, pH 6.8, 1.25% SDS, 10% glycerol, were incubated at 70° C. for 10 min before loading onto the stacking gel (4%), followed by electrophoresis at 12 mA for 2 h using the buffer system of Laemmli, Nature 227: 680 (1970). After electrophoresis, gels were washed for 1 h in 2.5% Triton X-100, then rinsed and incubated in 0.1M Tris, pH 8.0, for 18 h at 37° C. Gels were stained by immersion in 0.25% coomassie blue R-250 in 50% methanol/7% acetic acid for 60 min, then destained for 2 h in 30% methanol/10% acetic acid.

Detection of t-PA.mRNA

Total monocyte RNA was prepared according to the methods of Chirgwin et al. (1979) Biochemistry 18: 5292) and fractionated (5 μg/lane) on a formaldehyde-containing 1% agarose gel prior to transfer to Genescreen Plus nylon membrane (Dupont, Boston, Mass.). The filter was hybridized overnight at 60° C. in a standard hybridization buffer containing $>2 \times 10^6$ cpm/ml of $^{32}$P-labelled t-PA.cRNA. The cRNA probe was prepared from a plasmid containing the 2.3 kb Bgl II fragment from pPAll 4B (Fisher, R. et al. (1985) J. Biol. Chem. 260: 11223), cloned into the vector pGEM-4 blue (Promega, Madison, Mass.) and linearized with XbaI prior to initiation of transcription with T7 RNA polymerase (New England Biolabs, Beverly, Mass.). After hybridization, the filter was washed three times with $2 \times$ SSC prior to treatment with 1 μg/ml RNase A (Boehringer-Mannheim, West Germany) for 20 min at 37° C.

Measurement of Procoagulant Activity

Monocyte procoagulant activity is measured by the ability of the cells to shorten the partial thromboplastin (clotting) time of platelet poor plasma. The human monocytes ($4 \times 10^6$ cells/ml) are activated by lipopolysaccharide or a supernatant from stimulated lymphocytes for 18 h at 37° C. to generate procoagulant activity on their surface. This activity of frozen-thawed and sonicated cell samples was tested using citrate-treated platelet Poor human plasma in a prothrombin assay. Briefly, the clotting assay was performed by incubating the cell suspension $0.8 \times 10^5$ cells/0.1 ml) with 0.1 ml plasma for 1 min. at 37° C. Then CaCl$_2$ (30 mM; 0.1 ml) was added and the clotting time determined manually. Results are cited as mU of activity/$10^6$ cells. A standard curve of the clotting time of human plasma with decreasing dilutions of rabbit brain thromboplastin was used to calculate mU.

EXAMPLE 2 t-PA Production by IL-4 Stimulated Human Monocytes

Human monocytes prepared according to Example 1 ($1 \times 10^6$/ml) were incubated with 0.25 U/ml human recombinant IL-4 (Genzyme).

Plasminogen activator (PA) activity (determined by plasminogen-dependent fibrinolytic activity as described in Example 1) was detected in monocyte lysates after exposure to IL-4 for 2 h, and was secreted into the culture supernatants by 3 h, with maximal production of PA occurring 6 h after IL-4 stimulation.

All of the PA activity detected in the monocyte culture supernatants was blocked by anti-tPA IgG, but not by anti-urokinase IgG. By SDS-casein zymography, a technique which determines the apparent molecular weight of PA, a 70 kD band migrating in a manner characteristic of the t-PA standard was found. Accordingly, IL-4 stimulates human monocytes to produce t-PA.

Northern analysis showed the presence of t-PA.mRNA in monocytes treated with IL-4. t-PA mRNA was not detected in unstimulated monocytes.

EXAMPLE 3

Production of PA Activity by Endothelial Cells Stimulated with IL-4

Bovine aortic endothelial cells ($10^5$ cells) were incubated in RPMI/10% FCS for 48 h, washed in isotonic saline, and then cultured in $\alpha$-MEM (1 ml) in the presence or absence of 2.5 units/ml purified human IL-4 (Genzyme). After 24 h, conditioned medium was collected and assayed for PA activity, as a plasminogen-dependent fibrinolytic activity. PA activity was detected in those cells stimulated with IL-4. Results are as follows:

|  | PA Activity Iu/ml |
|---|---|
| Bovine endothelial cells (Control) | 0.09 ± 0.01 |
| Bovine endothelial cells stimulated with 2.5 units/ml | 0.32 ± 0.01 |

IL-4SDS-casein zymography identified urokinase type PA activity and t-PA activity with the increase being in the urokinase type.

EXAMPLE 4

Inhibition of Procoagulant Activity of Human Monocytes by IL-4

Human monocytes ($4 \times 10^6$ cells), prepared according to Example 1, were incubated with 100 ng/ml lipopolysaccharide (LPS), with human recombinant IL-4 (Schering Plough), or with LPS together with varying concentrations of IL-4.

Procoagulant activity (PCA) (determined by the shortening of the clotting time of citrated plasma as described in Example 1) was measured in monocyte lysates after exposure to the reagents for 18 h at room temperature.

| | PCA MU/$10^6$ cells | |
|---|---|---|
| | Experiment 1 | Experiment 2 |
| Human monocytes (control) | N.D. | N.D. |
| Human monocytes treated with 2.5 units/ml IL-4 | N.D. | N.D |
| Human monocytes treated with: | | |
| LPS (100ng/ml) | 20.9 ± 0.8 | 19.4 ± 0.5 |
| LPS (100ng/ml) + IL-4 (2.5 U/ml) | 4.6 ± 0.1 | 1.4 ± 0.1 |
| LPS (100ng/ml) + 0.5 | 4.2 ± 0.2 | 5.1 ± 0.2 |
| LPS (100ng/ml) + 0.1 U/ml) | 13.9 ± 0.4 | 8.5 ± 0.7 |

N.D. = not detected.

The claims defining the invention are as follows:
We claim:

1. A method for degrading fibrin deposits and preventing the formation of such deposits associated with pathological conditions or which may lead to such conditions, which comprises administering to a subject in need of such treatment a therapeutically effective amount of IL-4 or a derivative thereof possessing IL-4 activity, optionally in association with one or more pharmaceutically acceptable carriers or excipients.

2. A method according to claim 1, wherein the pathological conditions treated are selected from deep vein thrombosis, pulmonary embolism, renal disease, hypertrophic keloid scars, coronary infarction, metastasis, inflammation, disseminated intravascular coagulation, atherosclerosis, rheumatoid arthritis, glomerulonephritis, systemic lupus erythematosis, autoimmune neuropathies, granulomatous disease, parasitic infection, allograft rejection, and other conditions associated with fibrin deposition.

3. A method according to claim 1, wherein the IL-4 or a derivative thereof is locally administered at or near the site of fibrin deposition.

4. A method according to claim 1, where the IL-4 or a derivative thereof is administered by intravenous, intramuscular, intranasal, intradermal, intraperitoneal, suppository or oral route.

5. A method according to claim 1, where the therapeutically effective amount of IL-4 or derivatives thereof is between about 0.1 $\mu$g to about 200 mg per Kg body weight of the subject to be treated.

6. A method according to claim 1, where the IL-4 or a derivative thereof is continually infused into a subject for a predetermined period.

7. A method according to claim 1, wherein the IL-4 or a derivative thereof is administered in conjunction with one or more thrombolytic agents or activators of thrombolytic agents selected from tPA, urokinase, streptokinase or prourokinase.

8. A method according to claim 1, wherein the IL-4 or a derivative thereof is administered in conjunction with one or more anticoagulant agents such as heparin, warfarin, asprin, anisindione, phenindone and bishydroxy coumarin.

9. A thrombolytic composition comprising IL-4 or a derivative thereof possessing IL-4 activity in association with a pharmaceutically acceptable carrier or excipient, and one or more thrombolytic agents or activators thereof selected from the group consisting of tPA, urokinase, prourokinase and streptokinase.

10. A thrombolytic composition according to claim 9, which additionally comprises one or more anticoagulant agents.

11. A thrombolytic composition according to claim 10, wherein the anticoagulant agents are selected from the group consisting of heparin, warfarin, aspirin, anisindone, phenindone and bishydroxy coumarin.

12. A thrmobolytic composition according to claims 9 or 10, which additionally comprises one or more vasodilators.

13. A composition according to claim 12, wherein the vasodilators are selected from the group consisting of nitriles, papaverine, nicotinic acid and cyclandelate.

* * * * *